(12) United States Patent
Yeh et al.

(10) Patent No.: US 6,200,798 B1
(45) Date of Patent: Mar. 13, 2001

(54) DEFECTIVE RECOMBINANT ADENOVIRUSES WITH INACTIVATED IVA2 GENE

(75) Inventors: Patrice Yeh, Paris; Michel Perricaudet, Ecrosnes; Cécile Orsini, Paris; Emmanuelle Vigne, Ivry sur Seine, all of (FR)

(73) Assignee: Rhone-Poulenc Rorer SA, Antony Cedex (FR)

( * ) Notice: Subject to any disclaimer, the term of this patent is extended or adjusted under 35 U.S.C. 154(b) by 0 days.

(21) Appl. No.: 08/809,476

(22) PCT Filed: Sep. 22, 1995

(86) PCT No.: PCT/FR95/01228

§ 371 Date: Mar. 21, 1997

§ 102(e) Date: Mar. 21, 1997

(87) PCT Pub. No.: WO96/10088

PCT Pub. Date: Apr. 4, 1996

(30) Foreign Application Priority Data

Sep. 27, 1994 (FR) .................................................. 94 11511

(51) Int. Cl.[7] .......................... C12N 15/63; C12N 15/00; A01N 43/04; A61K 31/70
(52) U.S. Cl. ...................... 435/320.1; 435/455; 435/456; 435/325; 514/44; 424/93.21
(58) Field of Search ........................... 424/93.21; 514/44; 435/320.1, 172.3, 455, 456, 325

(56) References Cited

U.S. PATENT DOCUMENTS 5,585,362 * 12/1996 Wilson et al. .......................... 514/44

FOREIGN PATENT DOCUMENTS 2 707 664    1/1995  (FR) .

OTHER PUBLICATIONS

Orkin et al., Report and Recommendations of the Panel to Assess the NIH Investment in Research on Gene Therapy, Dec. 7, 1995.*
Eck & Wilson, Goodman & Gilman's The Pharmacological Basis of Therapeutics, McGraw–Hill, Ninth Edition, Chapter 5, pp. 77–101, 1995.*
Winter et al., Journal of Virology, vol. 65, pp. 5250–5259, Abstract only, Oct. 1991.*
Chen et al., Molecular and Cellular Biology, vol. 14, pp. 676–685, Abstract only, Jan. 1994.*
E. Marshall (1995) Science 269: 1050–1055.*
Miller et al (1995) FASEB J. 9:190–199.*
Natarajan et al., Proximal and distal domains that control in vitro transcription of the adenovirus IVa2 gene, Proc. Natl. Acad. Sci. USA, 81, pp. 6290–6294 (1984).

* cited by examiner

Primary Examiner—Bruce R. Campell
Assistant Examiner—Jill D. Martin

(57) ABSTRACT

The present invention relates to new viral vectors derived from adenoviruses, their preparation and utilization in gene therapy. It relates particularly to defective recombinant adenoviruses wherein the Iva2 gene at least is inactivated.

26 Claims, 9 Drawing Sheets

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

CCTTAGCCCG GGCTAAGGCA TG    22

(2) INFORMATION FOR SEQ ID NO:2:

(i) SEQUENCE CHARACTERISTICS:
      (A) LENGTH: 61 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:2:

TCGACGGATC CCTTAAGGTT GACGCCGCCA CCATGGAAAC CAGAGGGCGA AGACCGGCAG    60

C    61

DEFECTIVE RECOMBINANT ADENOVIRUSES WITH INACTIVATED IVA2 GENE

This 371 application claims the benefit of copending PCT/FR95/01228, filed Sep. 22, 1995.

BACKGROUND OF THE INVENTION

The present invention relates to new viral vectors, their preparation and their use in gene therapy. It also relates to the pharmaceutical compositions containing the said viral vectors. More particularly, the present invention relates to recombinant adenoviruses as vectors for gene therapy.

Gene therapy consists in correcting a deficiency or an abnormality (mutation, aberrant expression and the like) by the introduction of a genetic information into the cell or affected organ. This genetic information can be introduced either in vitro or in a cell extracted from the organ, the modified cell then being reintroduced into the body, or directly in vivo into the appropriate tissue. In this second case, various techniques exist, among which various transfection techniques involving complexes of DNA and ΔEAE-dextran (Pagano et al., J. Virol. 1 (1967) 891), of DNA and nuclear proteins (Kaneda et al., Science 243 (1989) 375), of DNA and lipids (Felgner et al., PNAS 84 (1987) 7413), the use of liposomes (Fraley et al., J. Biol. Chem. 255 (1980) 10431) and the like. More recently, the use of viruses as vectors for the transfer of genes has appeared as a promising alternative to these physical transfection techniques. In this respect, various viruses have been tested for their capacity to infect certain cellular populations. In particular, the retroviruses (RSV, HMS, MMS and the like), the HSV virus, the adeno-associated viruses and the adenoviruses.

Among these viruses, adenoviruses present some advantageous properties for a use in gene therapy. Especially, they have a fairly broad host spectrum, are capable of infecting quiescent cells, do not integrate into the genome of the infected cell, and have not been associated to date with major pathologies in man. Adenoviruses are viruses with linear double-stranded DNA of a size of about 36 kb. Their genome comprises especially an inverted repeat sequence (ITR) at their end, an encapsidation sequence, early genes and late genes (cf FIG. 1). The principal early genes are the E1 (E1a and E1b), E2, E3 and E4 genes. The principal late genes are the L1 to L5 genes.

Given the properties of the abovementioned adenoviruses, the latter have already been used for the transfer of genes in vivo. To this end, various vectors derived from adenoviruses have been prepared, incorporating various genes (β-gal, OTC, a-1AT, cytokines and the like). In each of these constructs, the adenovirus was modified so as to render it incapable of replication in the infected cell. Thus, the constructs described in the prior art are adenoviruses from which there have been deleted the E1 (E1a and/or E1b) and optionally E3 regions at the level of which the heterologous DNA sequences are inserted (Levrero et al., Gene 101 (1991) 195; Gosh-Choudhury et al., Gene 50 (1986) 161). Nevertheless, the vectors described in the prior art have numerous disadvantages which limit their exploitation in gene therapy. In particular, all these vectors contain numerous viral genes whose expression in vivo is not desirable within the framework of a gene therapy. Furthermore, these vectors do not permit the incorporation of very large DNA fragments which may be necessary for certain applications.

SUMMARY OF THE INVENTION

The present invention makes it possible to overcome these disadvantages. The present invention indeed describes new recombinant adenoviruses which can be used in gene therapy, especially for the transfer and expression of genes in vivo. In particular, the adenoviruses of the invention allow an efficient transfer and a lasting expression in vivo of a gene of interest, while limiting the risks of production of viral proteins, of transmission of the virus, of pathogenicity and the like.

The present invention consists more particularly in the construction of recombinant adinoviruses in which at least one specific viral gene, designated IVa2, has been made nonfunctional. The IVa2 gene is a small gene situated in the left-hand part of the adenovirus genome. It overlaps in part with the end of the E2B gene in particular, which makes its manipulation difficult. The IVa2 gene appears to play the role of activator of transcription of the late genes in the replicative cycle of the adenovirus. Its presence therefore allows or promotes the expression of the virus proteins which are necessary for the formation of the viral particles.

The applicant has now shown that it is possible to inactivate this gene in the adenovirus genome. The applicant has moreover shown that this inactivation does not affect the properties of the adenovirus as gene therapy vector, namely its high power to infect cells, especially human cells, and its capacity to efficiently transfer a gene of interest into the said cells. Furthermore, compared with the prior art vectors, the vectors described in the present invention have an improved capacity to incorporate genes of interest resulting from the inactivation, by deletion, of the IVa2 gene, and are in particular substantially less immunogenic since the expression of the late genes which may be present in the recombinant adenoviruses according to the invention is considerably reduced or even abolished.

The vectors of the invention are therefore particularly advantageous since they allow the incorporation of genes of interest of large size (greater than 8 kb and capable of growing up to more than 11 kb) without particularly affecting the titers obtained, and since they possess very few expressed viral regions, which substantially reduces or even suppresses the risks inherent in the use of viruses as vectors in gene therapy such as immunogenicity, pathogenicity, transmission, replication, recombination and the like. The present invention thus provides viral vectors which are particularly adapted to the transfer and expression in vivo of desired DNA sequences.

A first subject of the present invention therefore relates to a defective recombinant adenovirus in which the IVa2 gene at least is inactivated.

The adenoviruses are said to be defective when they are incapable of replicating autonomously in the infected cells. Generally, the genome of the adenoviruses according to the present invention is therefore devoid of at least the sequences necessary for the replication of the said virus in the infected cell. These regions can be either removed (completely or partly), or rendered nonfunctional, or substituted by other sequences and especially by a heterologous nucleic acid sequence.

As indicated above, the applicant has now shown that it is possible to inactivate the IVa2 gene in the genome of the adenovirus without affecting the desired properties of this virus. More particularly, for the preparation of the vectors of the invention, the IVa2 gene can be inactivated by various techniques known to persons skilled in the art, and especially by suppression, substitution, deletion and/or addition of one or more bases. Such modifications can be obtained in vitro (on isolated DNA) or in situ, for example, by means of genetic engineering techniques, or alternatively by treating with mutagenic agents. The said genetic modification(s) may be localized in the coding part of the gene, or outside the coding region, and for example in the regions responsible for the expression and/or transcriptional regulation of the said genes. The inactivation of the gene may therefore manifest itself by the production of an inactive protein because of structural or conformational modifications, by the absence of production, by the production of a protein having an altered activity, or alternatively by the production of the natural protein at an attenuated level or according to a desired mode of regulation.

Among the mutagenic agents which can be used for inactivation, there may be mentioned for example physical agents such as energetic radiations (X-, γ- and ultraviolet rays and the like), or chemical agents capable of reacting with various functional groups of the bases of the DNA, and for example alkylating agents [ethyl methanesulphonate (EMS), N-methyl-N'-nitro-N-nitrosoguanidine, N-nitroquinoline-1-oxide (NQO)], bialkylating agents, intercalating agents and the like.

The genetic modifications can also be obtained by gene disruption, for example according to the procedure initially described by Rothstein [Meth. Enzymol. 101 (1983) 202]. In this case, all or part of the coding sequence is preferably perturbed so as to permit the replacement, by homologous recombination, of the genomic sequence by a nonfunctional or mutant sequence.

Preferably, in the adenoviruses of the invention, the IVa2 gene is inactivated by mutation and/or deletion of one or more bases. Still more preferably, the IVa2 gene is inactivated by complete or partial deletion.

More particularly, deletion is understood to mean any suppression of all or part of the gene considered. This may be especially all or part of the coding region of the said gene, and/or all or part of the promoter region for transcription of the said gene. The suppression can be carried out by digestion by means of appropriate restriction enzymes, and then ligation, according to conventional molecular biology techniques, as illustrated in the examples.

In a particularly preferred manner, the inactivation of the genes is performed such that it affects only the considered gene and not the other viral genes, especially the neighbouring genes. Moreover, some alterations such as point mutations being, by nature, capable of being corrected or attenuated by cellular mechanisms, it is particularly preferred that the inactivation is perfectly stable segregationally and/or nonreversible.

According to a particularly advantageous mode, in the recombinant adenoviruses of the present invention, the IVa2 gene is inactivated by deletion of a BssHII-BstEII fragment extending from nucleotide 4106 to nucleotide 5186, on the Ad5 adenovirus sequence. This sequence is accessible in the literature and also on a database (see especially Genebank No. M73260).

The recombinant adenoviruses according to the invention advantageously comprise the ITR sequences and a region allowing encapsidation.

The inverted repeat sequences (ITR) constitute the replication origin of the adenoviruses. They are localized at the 3' and 5' ends of the viral genome (cf FIG. 1), from where they can be easily isolated according to conventional molecular biology techniques known to persons skilled in the art. The nucleotide sequence of the ITR sequences of human adenoviruses (in particular of the Ad2 and Ad5 serotypes) is described in the literature, as well as of canine adenoviruses (especially CAV1 and CAV2). As regards the Ad5 adenovirus for example, the left-hand ITR sequence corresponds to the region comprising nucleotides 1 to 103 of the genome.

The encapsidation sequence (also designated Psi sequence) is necessary for the encapsidation of the viral genome. This region should therefore be present in order to permit the preparation of defective recombinant adenoviruses according to the invention. The encapsidation sequence is localized in the genome of adenoviruses, between the left-hand (5') ITR and the E1 gene (cf FIG. 1). It can be isolated or synthesized artificially by conventional molecular biology techniques. The nucleotide sequence of the encapsidation sequence of human adenoviruses (in particular of the Ad2 and Ad5 serotypes) is described in the literature, as well as of canine adenoviruses (especially CAV1 and CAV2). As regards the Ad5 adenovirus, for example, a functional encapsidation sequence is present between nucleotides 194 and 358 of the genome.

In a first specific embodiment, the recombinant adenoviruses of the invention carry a deletion in relation to all or part of the E1 and IVa2 genes.

In another specific embodiment, the recombinant adenoviruses of the invention carry a deletion in relation to all or part of the E4 and IVa2 genes.

Still according to a preferred embodiment, the recombinant adenoviruses of the invention carry a deletion in relation to all or part of the E1, IVa2 and E3 genes.

In a particularly advantageous variant, the recombinant adenoviruses of the invention carry a deletion in relation to all or part of the E1, IVa2 and E4 genes.

Recombinant adenoviruses according to the invention having properties which are particularly attractive for use in gene therapy are those carrying a deletion in relation to all or part of the E1, IVa2, E3, E4 and possibly L5 genes. These vectors indeed combine properties in relation to infection, safety and gene transfer capacity which are very high.

Advantageously, the recombinant adenoviruses of the invention contain, in addition, a heterologous nucleic acid sequence whose transfer and/or expression in a cell, an organ or an organism is desired.

In particular, the heterologous DNA sequence may contain one or more therapeutic genes and/or one or more genes encoding antigenic peptides.

The therapeutic genes which can thus be transferred are any gene whose transcription and possibly translation in the target cell generate products having a therapeutic effect.

This may be in particular genes encoding protein products having a therapeutic effect. The protein product thus encoded may be a protein, a peptide, an amino acid and the like. This protein product may be hololgous with respect to the target cell (that is to say a product which is normally expressed in the target cell when the latter presents no pathology). In this case, the expression of a protein makes it possible for example to palliate an insufficient expression in the cell or the expression of an inactive or weakly active protein as a result of a modification, or alternatively to overexpress the said protein. The therapeutic gene may also encode a mutant of a cellular protein, having an increased stability, a modified activity and the like. The protein product may also be heterologous with respect to the target cell. In this case, an expressed protein can for example supplement or provide an activity deficient in the cell which enables it to combat a pathology.

Among the therapeutic products for the purposes of the present invention, there may be mentioned more particularly enzymes, blood derivatives, hormones, lymphokines: interleukins, interferons, TNF and the like (FR 9203120), growth factors, neurotransmitters or their precursors or synthetic enzymes, trophic factors: BDNF, CNTF, NGF, IGF, GMF, aFGF, bFGF, NT3, NT5 and the like; apolipoproteins: ApoAI, ApoAIV, ApoE and the like (FR 93 05125), dystrophin or minidystrophin (FR 9111947), tumour suppressor genes: p53, Rb, Rap1A, DCC, k-rev and the like (FR 93 04745), genes encoding factors involved in coagulation: Factors VII, VIII, IX and the like, suicide genes: thymidine kinase, cytosine deaminase and the like.

The therapeutic gene can also be an antisense gene or sequence, whose expression in the target cell makes it possible to control the expression of genes or the transcription of cellular mRNAs. Such sequences can for example be transcribed, in the target cell, into RNAs which are complementary to cellular mRNAs and thus block their translation into protein, according to the technique described in Patent EP 140 308.

As indicated above, the heterologous DNA sequence may also contain one or more genes encoding an antigenic peptide, capable of generating an immune response in man. In this particular implementational embodiment, the invention therefore permits the production of vaccines which make it possible to immunize man, especially against microorganisms or viruses. These may be especially antigenic peptides specific for the Epstein Barr virus, the HIV virus, the hepatitis B virus (EP 185 573), the pseudo-rabies virus, or alternatively specific for tumours (EP 259 212).

Generally, the heterologous nucleic acid sequence also comprises a promoter region for transcription which is functional in the infected cell. This may be a promoter region which is naturally responsible for the expression of the considered gene when this region is capable of functioning in the infected cell. This may also be regions of different origin (which are responsible for the expression of other proteins, or even synthetic). In particular this may be promoter sequences of eucaryotic or viral genes. For example, this may be promoter sequences derived from the genome of the cell which it is desired to infect. Likewise, this may be promoter sequences derived from the genome of a virus, including the adenovirus used. In this respect, there may be mentioned, for example, the promoters of the E1A, MLP, CMV, RSV genes and the like. In addition, these promoter regions can be modified by addition of activating sequences, regulatory sequences, or sequences permitting a predominant or tissue-specific expression. Moreover, when the heterologous nucleic acid does not contain promoter sequences, it can be inserted into the geonome of the defective virus downstream of such a sequence.

Furthermore, the heterologous nucleic acid sequence may also contain, in particular upstream of the therapeutic gene, a signal sequence directing the therapeutic product synthesized in the secretory pathways of the target cell. This signal sequence may be the natural signal sequence of the therapeutic product, but it may also be any other functional signal sequence, or an artificial signal sequence.

Still in a particularly advantageous mode, the vectors of the invention possess, in addition, a functional E3 gene under the control of a heterologous promoter. More preferably, the vectors possess part of the E3 gene which allows the expression of the gp19K protein. This protein in fact makes it possible to avoid the adenovirus vector becoming the object of an immune reaction which (i) could limit its action and (ii) could have undesirable side effects.

The recombinant adenoviruses according to the invention may be of various origins. There are various adenovirus serotypes whose structure and properties vary somewhat, but which exhibit a comparable genetic organization. Because of this, the teachings described in the present application can be easily reproduced by persons skilled in the art for any type of adenovirus.

More particularly, the adenoviruses of the invention may be of human, animal or mixed (human and animal) origin.

As regards the adenoviruses of human origin, the use of those classified in group C is preferred. More preferably, among the various human adenovirus serotypes, the use of the type 2 or 5 adenoviruses (Ad2 or Ad5) is preferred within the framework of the present invention.

As indicated above, the adenoviruses of the invention may also be of animal origin, or contain sequences derived from adenoviruses of animal origin. The Applicant has indeed shown that the adenoviruses of animal origin are capable of infecting, with a high efficiency, human cells, and that they are incapable of propagating in the human cells in which they were tested (cf. Application FR 93 05954). The Applicant also showed that the adenoviruses of animal origin are not at all transcomplemented by adenoviruses of human origin, which eliminates any risk of recombination and of propagation in vivo, in the presence of a human adenovirus, capable of leading to the formation of an infectious particle. The use of adenoviruses or of adenovirus regions of animal origin is therefore particularly advantageous since the risks inherent in the use of viruses as vectors in gene therapy are even smaller.

The adenoviruses of animal origin which can be used within the framework of the present invention may be of canine, bovine, murine, (example: Mavl, Beard et al., Virology 75 (1990) 81), ovine, procine or avian or alternatively simian origin (example: SAV). More particularly, among the avian adenoviruses, there may be mentioned the serotypes 1 to 10 which are available at ATCC, such as for example the strains Phelps (ATCC VR-432), Fontes (ATCC VR-280), P7-A (ATCC VR-827), IBH-2A (ATCC VR-828), J2-A (ATCC VR-829), T8-A (ATCC VR-830), K-11 (ATCC VR-921) or alternatively the strains referenced ATCC VR-831 to 835. Among the bovine adenoviruses, the various known serotypes can be used, and especially those available at ATCC (types 1 to 8) under the references ATCC VR-313, 314, 639–642, 768 and 769. There may also be mentioned the murine adenoviruses FL (ATCC VR-550) and E20308 (ATCC VR-528), the type 5 (ATCC VR-1343), or type 6 (ATCC VR-1340) ovine adenovirus; the porcine adenovirus (5359), or the simian adenoviruses such as especially the adenoviruses referenced at ATCC under the numbers VR-591–594, 941–943, 195–203 and the like.

Preferably, among the various adenoviruses of animal origin, adenoviruses or adenovirus regions of canine origin, and especially all the CAV2 adenovirus strains [manhattan or A26/61 strain (ATCC VR-800) for example] are used within the framework of the invention. The canine adenoviruses have been the subject of numerous structural studies. Thus, complete restriction maps of the CAV1 and CAV2 adenoviruses have been described in the prior art (Spibey et al., J. Gen. Virol, 70 (1989) 165), and the E1a and E3 genes as well as the ITR sequences have been cloned and sequenced (see especially Spibey et al., Virus Res. 14 (1989) 241; Linné, Virus Res. 23 (1992) 119, WO 91/11525).

The defective recombinant adenoviruses according to the invention can be prepared in various ways.

A first method consists in transfecting the DNA from the defective recombinant virus prepared in vitro (either by ligation, or in plasmid form) into a competent cell line, that is to say carrying in trans all the functions necessary for the complementation of the defective virus. These functions are preferably integrated in the genome of the cell, which reduces the risks of recombination, and confers increased stability on the cell line. The preparation of such cell lines is described in the examples.

A second approach consists in cotransfecting, into an appropriate cell line, the DNA from the defective recombinant virus prepared in vitro (either by ligation, or in plasmid form) and the DNA from one or more helper viruses or plasmids. According to this method, it is not necessary to have a competent cell line capable of complementing all the defective functions of the recombinant adenovirus. Part of these functions is indeed complemented by the helper virus (es). This or these helper viruses are themselves defective. The preparation of defective recombinant adenoviruses of the invention according to this method is also illustrated in the examples.

In this respect, the present application also describes the construction of plasmids carrying the modified left-hand part of the Ad5 adenovirus genome (plasmids pCO1 and pCO2). These plasmids are particularly useful for the construction of defective recombinant adenoviruses as vectors for gene therapy. Thus, the plasmid pCO1 carries the left-hand region of the adenovirus genome, from the left-hand ITR up to nucleotide 6316, with a deletion of the region between nucleotides 382–3446, corresponding to the E1 gene. This plasmid is particularly advantageous since it carries, compared with the other plasmids of this type which are described in the prior art, a greater deletion in the E1 gene, which offers greater cloning capacity and, especially, fewer risks of recombination. The plasmid pCO2 is derived from the plasmid pCO1 by deletion of an additional region between nucleotides 4106–5186, and corresponding to part of the IVa2 gene. This deletion has the advantage of not affecting the E2 gene. The plasmid pCO6 derives from the plasmid PCO1 by insertion of a stop codon into the reading frame of the IVa2 gene. Plasmids pCO1, pCO2 and pCO6 contain, moreover, a multiple cloning site allowing the incorporation of a heterologous nucleic acid sequence of interest. The resulting construct can then be used to prepare the defective recombinant adenovirus by cotransfection with a DNA corresponding to the right-hand part of the adenovirus genome into a competent cell line. As regards the latter, it may be derived from the genome of a wild-type virus, or of a virus which is itself defective, such as Addl324 which is deleted of the E3 region, and Addl808 which is deleted of the E4 region (Weinberg et al., J. Virol. 57 (1986) 833), and the like (cf examples). Among the cell lines which can be used, there may be mentioned especially the human embryonic kidney line 293, KB cells, Hela cells, MDCK, GHK and the like, and more generally, any cell line which complements the deleted regions (cf examples).

Next, the recombinant viruses which have multiplied are recovered, purified and amplified according to conventional virology techniques.

The plasmid pCO1 thus allows the construction of defective recombinant adenoviruses carrying a deletion in the E1 gene extending from nucleotide 382 to nucleotide 3446.

The plasmid pCO2 allows the construction of defective recombinant adenoviruses carrying a deletion in the E1 gene, extending from nucleotide 382 to nucleotide 3446, and a deletion in the IVa2 gene, extending from nucleotide 4106 to nucleotide 5186.

The plasmid pCO6 allows the construction of defective recombinant adenoviruses having a deletion in the E1 gene, ranging from nucleotide 382 to nucleotide 3446, and whose IVa2 gene has been inactivated by insertion of a stop codon into its reading frame, at the level of the Sph1 site corresponding to base 5141 of the Ad5 adenovirus.

The present invention also describes a series of plasmids allowing the construction of cell lines transcomplementing the defective recombinant adenoviruses. In particular, the plasmid pAC5 which possesses the IVa2 gene under the control of its own promoter and the plasmids pGY37-TK-IVa2 and pGY37-CMV-IVa2 which carry the IVa2 gene under the control of the TK and CMV promoters respectively. These plasmids also carry the EBNA1/OriP sequences which allow them to replicate in eukaryotic cells. These plasmids therefore allow the construction of cell lines which transcomplement the defective recombinant adenoviruses for the Iva2 gene without the need to use a helper virus.

The present invention also relates to any pharmaceutical composition comprising one or more defective recombinant adenoviruses as described above. The pharmaceutical compositions of the invention can be formulated for a topical, oral, parenteral, intranasal, intravenous, intramuscular, subcutaneous, intraocular and transdermal administration and the like.

Preferably, the pharmaceutical composition contains vehicles which are pharmecutically acceptable for an injectable formulation. These may be in particular saline (monosodium or disodium phosphate, sodium, potassium, calcium or magnesium chloride and the like or mixtures of such salts), sterile or isotonic solutions, or dry, especially freeze-dried, compositons, which by addition, depending on the case, of sterilized water or physiological saline, permit the constitution of injectable solutions.

The virus doses used for the injection can be adapted as a function of various parameters, and especially as a function of the mode of administration used, the relevant pathology, the gene to be expressed, or alternatively the desired duration of the treatment. Generally, the recombinant adenoviruses according to the invention are formulated and administered in the form of doses of between $10^4$ and $10^{14}$ pfu, and preferably $10^6$ to $10^{10}$ pfu. The term pfu ("plaque forming unit") corresponds to the infectivity of a virus solution, and is determined by infecting an appropriate cell culture, and measuring, generally after 5 days, the number of plaques of infected cells. The techniques for the determination of the pfu titer of a viral solution are well documented in the literature.

Depending on the inserted heterologous DNA sequence, the adenoviruses of the invention can be used for the treatment or prevention of numerous pathologies including genetic diseases (dystrophy, cystic fibrosis and the like), neurodegenerative diseases (Alzheimer, Parkinson, ALS and the like), cancers, pathologies linked to coagulation disorders or to dyslipoproteinaemias, pathologies linked to viral infections (hepatitis, AIDS and the like) and the like.

The present invention will be more fully described with the aid of the following examples which should be considered as illustrative and non-limiting.

DETAILED DESCRIPTION OF THE INVENTION

Figure 1:
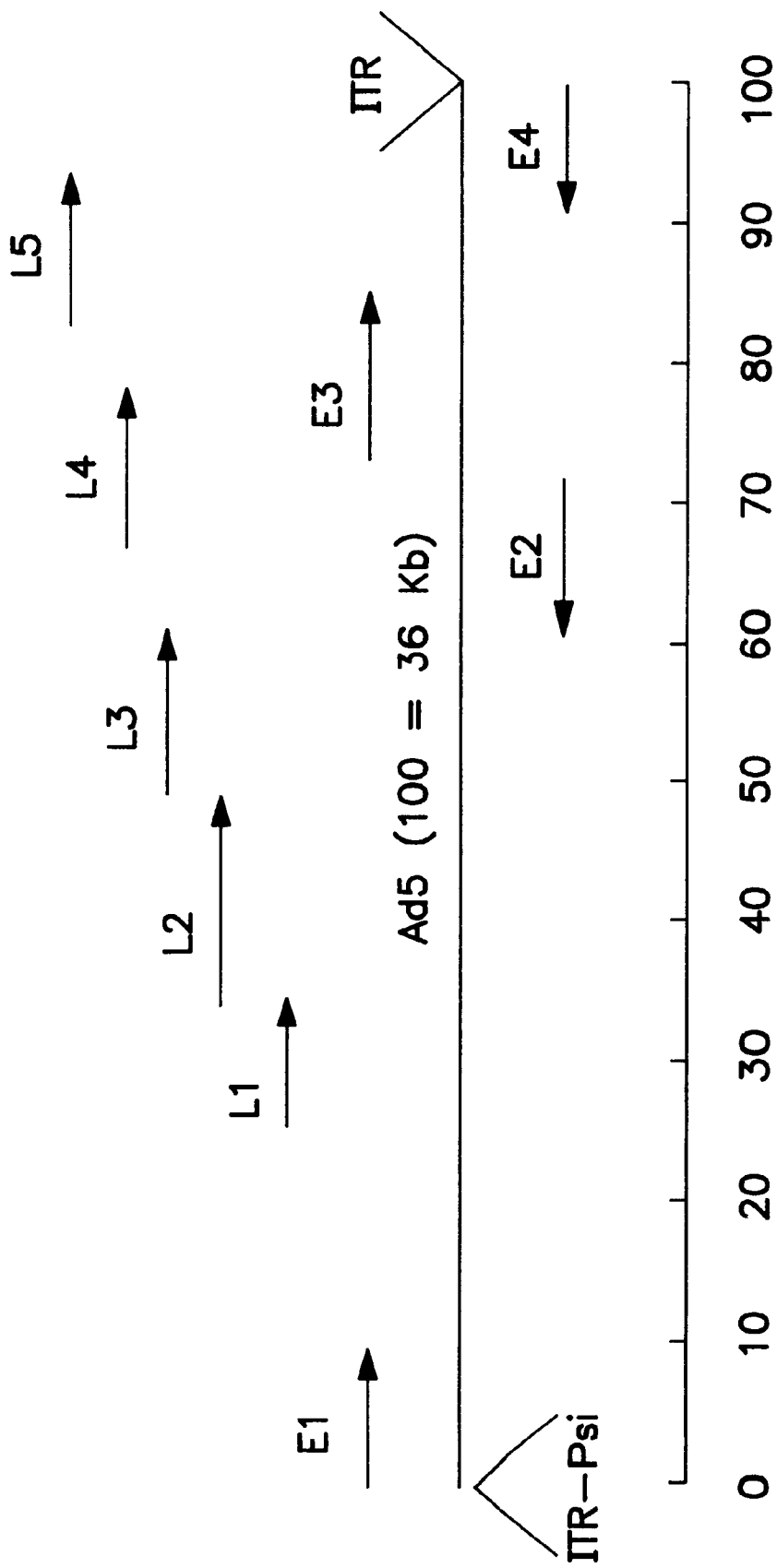
FIG. 1: Genetic organization of the Ad5 adenovirus. The complete sequence of Ad5 is available on database and enables persons skilled in the art to select or create any restriction site, and thus to isolate any region of the genome.
Figure 2:
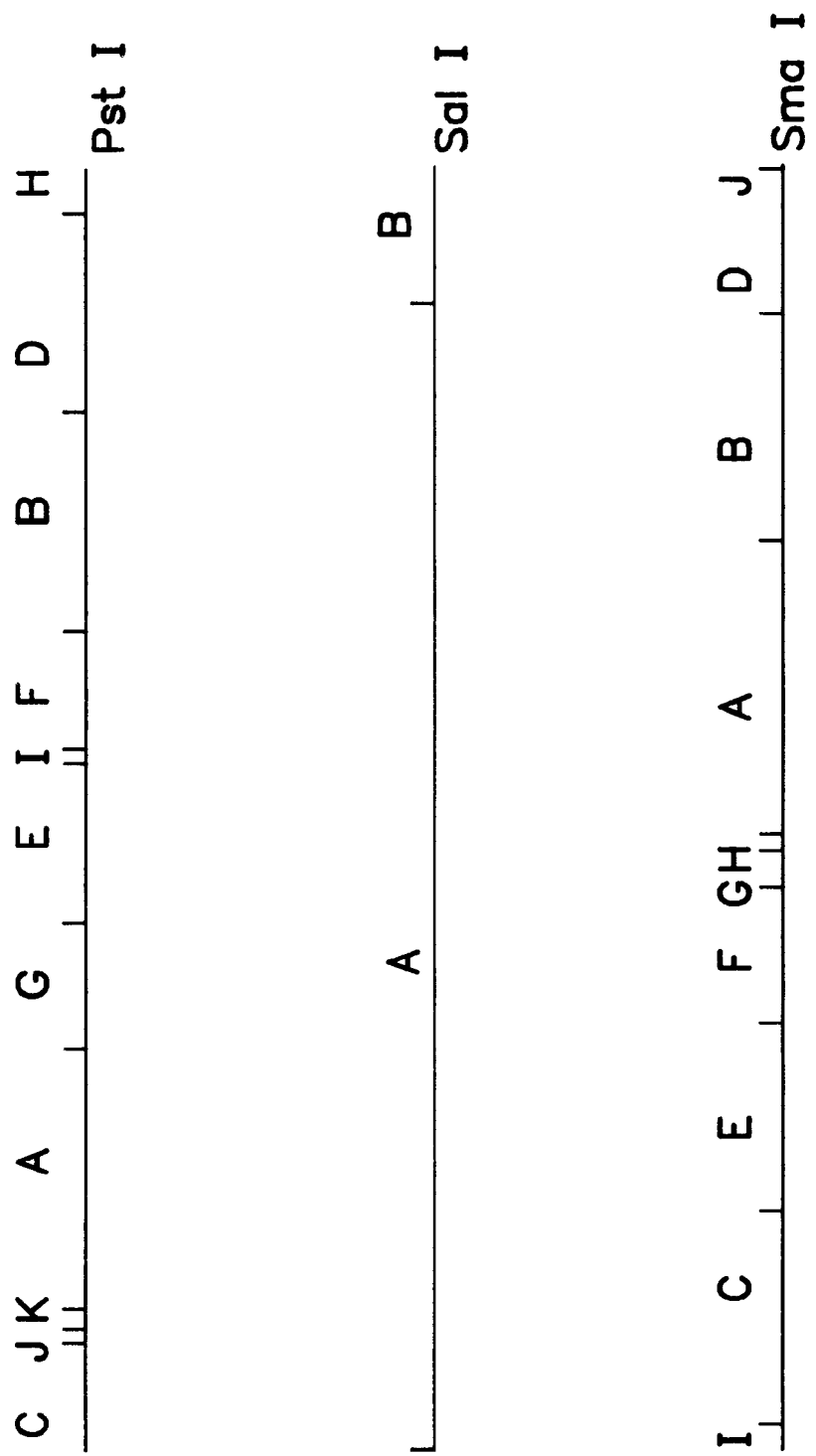
FIG. 2: Restriction map of the CAV2 adenovirus Manhattan strain (according to Spibey et al., previously cited).

The conventional methods used in molecular biology such as preparative extractions of plasmid DNA, centrifugation of plasmid DNA in cesium chloride gradient, electrophoresis on agarose or acrylamide gels, purification of DNA fragments by electroelution, protein extractions with phenol or phenol-chloroform, DNA precipitation in saline medium with ethanol or isopropanol, transformation in *Escherichia coli* and the like, are well known to persons skilled in the art and are widely described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

The pBR322 and pUC type plasmids and the phages of the M13 series are of commercial origin (Bethesda Research Laboratories).

For the ligations, the DNA fragments can be separated according to their size by agarose or acrylamide gel electrophoresis, extracted with phenol or with a phenol/chloroform mixture, precipitated with ethanol and then incubated in the presence of phage T4 DNA ligase (Biolabs) according to the recommendations of the supplier.

The filling of the protruding 5' ends can be performed with the Klenow fragment of DNA polymerase I of *E. coli* (Biolabs) according to the specifications of the supplier. The destruction of the protruding 3' ends is performed in the presence of phage T4 DNA polymerase (Biolabs) which is used according to the recommendations of the manufacturer. The destruction of the protruding 5' ends is performed by a controlled treatment with S1 nuclease.

The site-directed mutagenesis in vitro with synthetic oligodeoxynucleotides can be carried out according to the method developed by Taylor et al. [Nucleic Acids Res. 13 (1985) 8749–8764] using the kit distributed by Amersham.

The enzymatic amplification of DNA fragments by the so-called PCR technique [Polymerase-catalyzed Chain Reaction, Saiki R. K. et al., Science 230 (1985) 1350–1354; Mullis K. B. and Faloona F. A., Meth. Enzym. 155 (1987) 335–350] can be carried out using a "DNA thermal cycler" (Perkin Elmer Cetus) according to the specifications of the manufacturer.

The verification of the nucleotide sequences can be carried out by the method developed by Sanger et al. [Proc. Natl. Acad. Sci. USA, 74 (1977) 5463–5467] using the kit distributed by Amersham.

Cell Lines Used

In the following examples, the following cell lines were or can be used:

Human embryonic kidney line 293 (Graham et al., J. Gen. Virol. 36 (1977) 59). This line contains especially, integrated in its genome, the left-hand part of the genome of the human adenovirus Ad5 (12%).

Human cell line KB: derived from a human epidermal carcinoma, this line is available at ATCC (ref. CCL17) as well as the conditions permitting its culture.

Human cell line Hela: derived from a carcinoma of the human epithelium, this line is available at ATCC (ref. CCL2) as well as the conditions permitting its culture.

Canine cell line MDCK: the conditions for culture of the MDCK cells have been described especially by Macatney et al., Science 44 (1988)9.

Cell line gm DBP6 (Brough et al., Virology 190 (1992) 624). This line consists of Hela cells carrying the adenovirus E2 gene under the control of the LTR of MMTV.

EXAMPLES

Example 1

Figure 3:
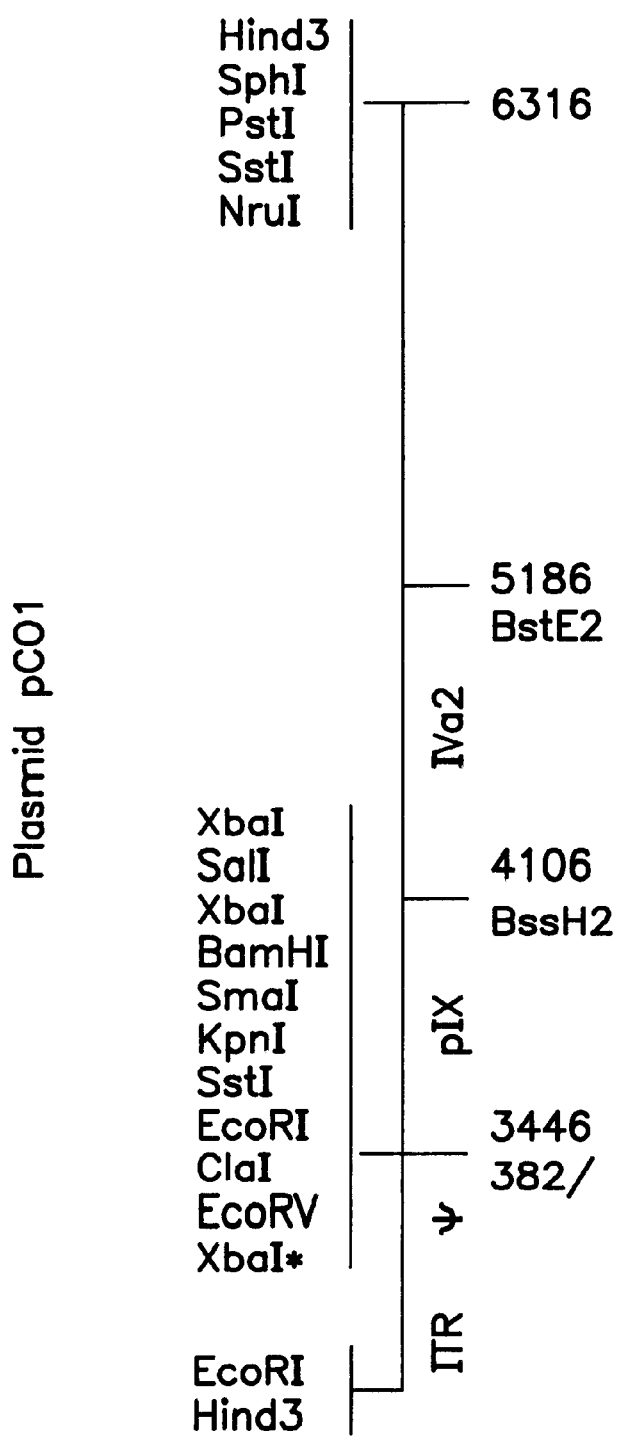
FIG. 3: Restriction map of the HindIII fragment contained in the plasmid pCO1.

Construction of the Plasmid pCO1 (FIG. 3)

A - Construction of the Plasmid pCE

The EcoRI-XbaI fragment corresponding to the left-hand end of the Ad5 adenovirus genome was first cloned between the EcoRI and XbaI sites of the vector pIC19H. This generates the plasmid pCA. The plasmid pCA was then cut with HinfI, its protruding 5' ends were filled with the klenow fragment of DNA polymerase I of *E. coli* and then it was cut with EcoRI. The fragment thus generated from the plasmid pCA, which contains the left-hand end of the Ad5 adenovirus genome, was then cloned between the EcoRI and SmaI sites of the vector pIC20H (Marsh et al., Gene 32 (1984) 481). This generates the plasmid pCB. The plasmid pCB was then cut with EcoRI, its protruding 5' ends were filled with the klenow fragment of DNA plymerase I of *E. coli* and then it was cut with BamHI. The fragment thus generated from the plasmid pCB, which contains the left-hand end of the Ad5 adenovirus genome, was then cloned between the NruI and BglII sites of the vector pIC20H. This generates the plasmid pCE of which an advantageous characteristic is that it has the first 382 base pairs of the Ad5 adenovirus which are followed by a multiple cloning site.

B - Construction of the Plasmid pCD'

The Sau3A (3346)—SstI (3645) fragment and the SstI (3645) - NarI (5519) fragment of the Ad5 adenovirus genome were first ligated and cloned between the ClaI and BamHI sites of the vector pIC20H, which generates the plasmid pPY53. The SalI-Taq-I fragment of the plasmid pPY53 prepared from a dam– context, containing the part of the Ad5 adenovirus genome between the Sau3A (3346) and TaqI (5207) sites, was then cloned between the SalI and ClaI sites of the vector pIC20H, which generates the plasmid pCA'. The TaqI (5207) - NarI (5519) fragment of the Ad5 adenovirus genome prepared from a dam– context and the SalI-TaqI fragment of the plasmid pCA' were then ligated and cloned between the SalI and NarI sites of the vector pIC20H. This generates the plasmid pCC'. The NarI (5519) - NruI (6316) fragment of the Ad5 adenovirus genome prepared from a dam– context and the SalI-NarI fragment of the plasmid pCC' were then ligated and cloned between the SalI and NruI sites of the vector pIC20R. This generates the plasmid pCD'.

C - Construction of the plasmid pCO1.

A partial digestion with XhoI and then a complete digestion with SalI of the plasmid pCD' generates a restriction fragment which contains the Ad5 adenovirus sequence, from the Sau3A (3446) site to the NruI (6316) site. This fragment was cloned into the SalI site of the plasmid pCE. This generates the plasmid pCO1 (FIG. 3), which contains the left-hand part of the Ad5 adenovirus up to the HinfI site (382), a multiple cloning site and the Sau3A (3446) - NruI (6316) fragment of the Ad5 adenovirus.

Example 2

Figure 4:
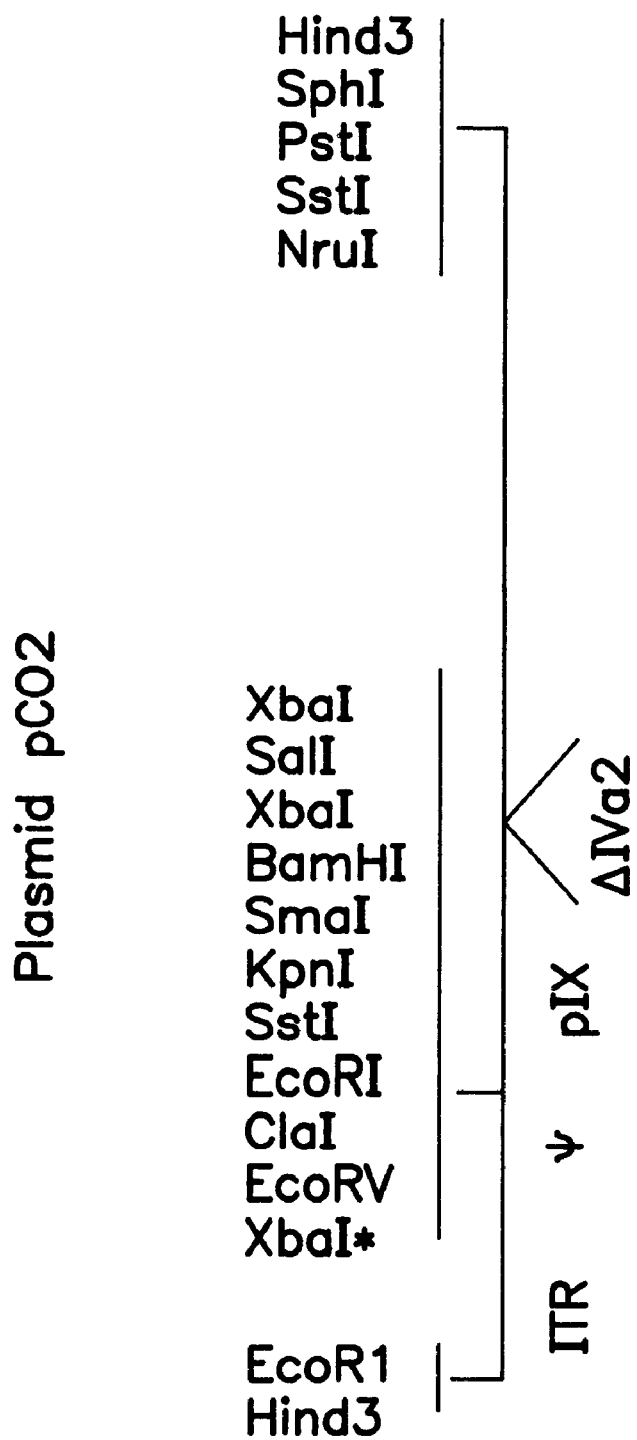
FIG. 4: Restrictoin map of the HindIII fragment contained in the plasmid pCO2.

Construction of the plasmid pCO2 (FIG. 4)

A—Construction of the plasmid pCD".

The BssHII-BstEII fragment corresponding to the BssHII (4106) - BstEII (5186) fragment of the Ad5 adenovirus genome was first removed from the plasmid pCA'. This generates the plasmid pCB", of which an advantageous characteristic is that it has a deletion in relation to part of the sequence of the IVa2 gene. The TaqI (5207) - NarI (5519) fragment of the Ad5 adenovirus genome prepared from a dam− context and the SalI-TaqI fragment of the plasmid pCB" were then ligated and cloned between the SalI and NarI sites of the vector pIC20H. This generates the plasmid pCC". The NarI (5519) - NruI (6316) fragment of the Ad5 adenovirus genome prepared from a dam− context and the SalI-NarI fragment of the plasmid pCC" were then ligated and cloned between the SalI and NruI sites of the vector pIC20R. This generates the plasmid pCD".

B—Construction of the plasmid pCO2.

A partial digestion of the XhoI and then a complete digestion with SalI of the plasmid pCD" generates a restriction fragment which contains the Ad5 adenovirus sequence, from the Sau3A (3446) site to the NruI (6316) site, whose BssHII (4106) - BstEII (5186) fragment has been deleted. This fragment was cloned into the SalI site of the plasmid pCE. This generates the plasmid pCO2 (FIG. 4), which contains the left-hand part of the Ad5 adenovirus up to the HinfI (382) site, a multiple cloning site and the Sau3A (3446) - NruI (6316) fragment of the Ad5 adenovirus, whose BssHII (4106) - BstEII (5286) fragment has been deleted.

Example 3

Construction of a recombinant adenovirus carrying a deletion in the E1 gene This example describes the construction of a defective recombinant adenovirus carrying a deletion in the E1 region extending from nucleotide 382 to nucleotide 3446. This adenovirus is particularly advantageous since it contains a greater deletion in the E1 gene, offering greater cloning capacity and, especially, fewer risks of recombination.

This recombinant adenovirus was obtained by recombination in vivo, by cotransfection into the cells 293, in the presence of calcium phosphate, DNA from the ADRSVβgal virus digested with ClaI and from the plasmid pCO1 digested with XmnI. The cells are then harvested, disrupted by three freeze-thaw cycles in their supernatant, and then centrifuged at 4000 rpm for 10 minutes. The supernatant thus obtained is then amplified on a fresh cell culture. The viruses are then purified from plaques and their DNA is analyzed according to the Hirt method (cited above). Virus stocks are then prepared on a cesium chloride gradient.

Example 4

Construction of a recombinant adenovirus carrying a deletion in the E1 and IVa2 genes This example describes the construction of a defective recombinant adenovirus carrying a deletion in the E1 region, extending from nucleotide 382 to nucleotide 3446, plus a deletion in the IVa2 region. This adenovirus is particularly advantageous since, compared with the adenovirus described in Example 3, it contains a deletion in the IVa2 gene, offering greater cloning capacity and, especially, fewer risks of production of viral proteins in vivo.

A—Construction of the defective recombinant adenovirus ΔE1-ΔVIa2 in cell lines transcomplementing the E1 function (E1+).

The recombinant adenovirus was prepared according to the following three procedures:

(a) The AdRSVβgal virus DNA digested with ClaI and the plasmid pCO2 digested with XmnI were cotransfected into the cells E1$^+$ (293 or 293 E4) in the presence of calcium phosphate, so as to allow in vivo recombination.

(b) The AdRSVβgal virus DNA digested with ClaI and with XcaI and the plasmid pCO2 digested with XmnI were cotransfected into the cells E1$^+$ (293 or 293 E4) in the presence of calcium phosphate, so as to allow in vivo recombination.

(c) The AdRSVβgal virus DNA and the plasmid pCO2 both digested with XcaI are first ligated in vitro and then the resulting construct is transfected into the cells E1$^+$ (293 or 293 E4) in the presence of calcium phosphate.

(d) The AdRSVβgal virus DNA digested with Cla1, the plasmid pCO2 DNA digested with Xmn1 and the DNA of the helper virus pAC2 were cotransfected into the cells E1$^+$ (293 or 293 E4) in the presence of calcium phosphate.

(e) The AdRSVβgal virus DNA digested with Cla1, the plasmid pCO6 DNA digested with Xmn1 and the DNA of the helper virus pAC2 were cotransfected into the cells E1$^+$ (293 or 293 E4) in the presence of calcium phosphate.

(The plasmids pAC2 and pCO6 are described in Example 7)

The viruses produced are then amplified and purified as in Example 3.

B—Construction of an adenovirus ΔE1-ΔIVa2 in cell lines transcomplementing the IVa2 function.

In the cell clones expressing the IVa2 region of the adenovirus Ad5, the adenovirus ΔE1-ΔIVa2 was able to be prepared according to the following two procedures:

(a) The AdRSVβgal virus DNA digested with Cla1 and the plasmid pCO2 DNA digested with Xmn1 were cotransfected into the cells in the presence of calcium phosphate.

(b) The AdRSVβgal virus DNA digested with Cla1 and the plasmid pCO6 DNA digested with Xmn1 were cotransfected into the cells in the presence of calcium phosphate.

Example 5

Construction of a recombinant adenovirus carrying a deletion in the E1, E3 and IVa2 genes This example describes the construction of a defective recombinant adenovirus carrying a deletion in the E1 region, extending from nucleotide 382 to nucleotide 3446, a deletion in the IVa2 gene, and a deletion in the E3 region. This adenovirus is particularly advantageous since, compared with the adenovirus described in Example 4 it contains a deletion in the E3 region, offering greater cloning capacity.

The recombinant adenovirus was prepared according to the following three procedures:

(a) The Add1324 virus DNA digested with ClaI and the plasmid pCO2 digested with XmnI were cotransfected into the cells 293 in the presence of calcium phosphate, so as to allow in vivo recombination.

(b) The Add1324 virus DNA digested with ClaI and with XcaI and the plasmid pCO2 digested with XmnI were cotransfected into the cells 293 in the presence of calcium phosphate, so as to allow in vivo recombination.

(c) the Add1324 virus DNA and the plasmid pCO2 both digested with XcaI are first ligated in vitro and then the resulting construct is transfected into the cells 293 in the presence of calcium phosphate.

The viruses produced are then amplified and purified as in Example 3.

Example 6

Construction of a recombinant adenovirus carrying a deletion in the E1, E3, E4 and IVa2 genes This example describes the preparation of a defective recombinant adenoviruses according to the invention from whose genome the IVa2, E1, E3 and E4 genes are deleted. These adenovirus possess, first of all, a large capacity to incorporate heterologous genes. Moreover, these vectors are highly safe because of the deletion of the IVa2 region and of the E4 region. The latter is indeed involved in the regulation of the expression of the late genes, in the processing of the late premessenger RNAs, in the extinction of the expression of the proteins of the host cell and in the efficiency of the replication of the viral DNA. These vectors therefore possess a transcriptional background noise and a viral gene expression which are likely reduced. Finally, in a particularly advantageous manner, these vectors can be produced at high titres.

The right-hand part of a viral genome, deleted in relation to the E3 and E4 regions (cf. section B), or only in relation to the E4 region as in the case of the viruses d1808, d11004, d11007 or d11010 described by G. Ketner for example (J. of Virology, 63 (1988) 631). According to another alternative, the right-hand part may contain deletions in several regions and for example in the E3 and E4 regions such as those constructed in vitro and presented in the virus prepared as follows from the plasmid pPY55.

A/Construction of the adenovirus deleted in the E1, E3 and E4 genes.

A.1 Construction of the plasmid pPY55.

a) Construction of the plasmid pPY32.

Figure 5:
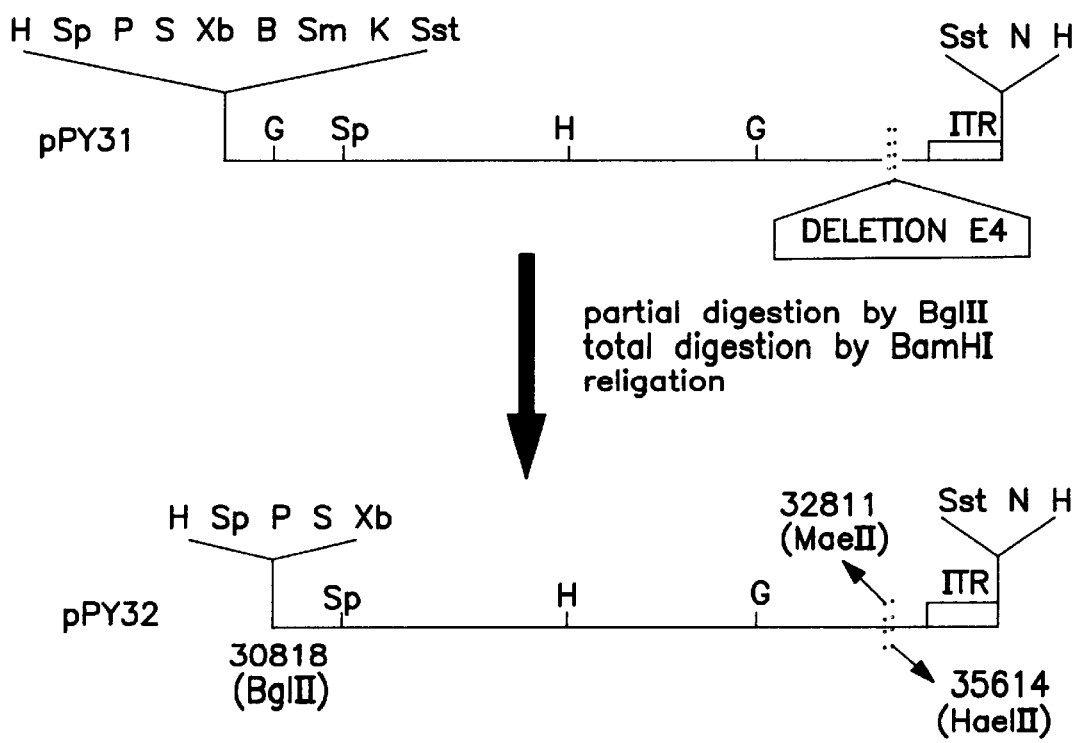
FIG. 5: Construction and representation of the plasmid pPY32.

The AvrII-BclII fragment of the plasmid pFG144 [F. L. Graham et al. EMBO J. 8(1989) 2077–2085], corresponding to the right-hand end of the genome of the Ad5 adenovirus, was first cloned between the XbaI and BamHI sites of the vector pIC19H, prepared from a dam– context. This generates the plasmid pPY23. One advantageous characteristic of the plasmid pPY23 is that the SalI site obtained from the multiple cloning site of the vector pIC19H remains unique and that it is localized beside the right-hand end of the genome of the Ad5 adenovirus. The HaeIII-SalI fragment of the plasmid pPY23 which contains the right-hand end of the genome of the Ad5 adenovirus. From the HaeIII site localized in position 35614, was then cloned between the EvoRV and XhoI sites of the vector pIC20H, which generates the plasmid pPY29. One advantageous characteristic of this plasmid is that the XbaI and ClaI sites obtained from the multiple cloning site of the vector pIC20H are localized beside the EcoRV/HaeIII junction resulting from the cloning. Furthermore, this junction modifies the nucleotide context immediately adjacent to the ClaI site which has now become methylatable in a dam+ context. The XbaI(30470)-MaeII(32811) fragment of the genome of the Ad5 adenovirus was then cloned between the XbaI and ClaI sites of the plasmid pPY29 prepared from a dam– context, which generates the plasmid pPY30. The SstI fragment of the plasmid pPY30, which corresponds to the sequence of the genome of the Ad5 adenovirus from the SstI site in position 30556 up to the right-hand end was finally cloned between the SstI sites of the vector pIC20H, which generates the plasmid pPY31, of which a restriction map of the insert localized between the HindIII sites is given in FIG. 5.

The plasmid pPY32 was obtained after partial digestion of the plasmid pPY31 with BglII, followed by a total digestion with BamHI, and then religation. The plasmid pPY32 therefore corresponds to the deletion in relation to the genome of the Ad5 adenovirus situated between the BamHI site of the plasmid pPY31 and the BglII site localized in position 30818. A restriction map of the HindIII fragment of the plasmid pPY32 is given in FIG. 5. One characteristic of the plasmid pPY32 is that it possesses unique SalI and XbaI sites.

Construction of the plasmid pPY47.

The BamHI (21562)-XbaI(28592) fragment of the genome of the Ad5 adenovirus was first cloned between the BamHI and XbaI sites of the vector pIC19H prepared from a damn– context, which generates the plasmid pPY17. This plasmid therefore contains a HindIII(26328) - BglII(28133) fragment of the genome of the Ad5 adenovirus, which can be cloned between the HindIII and BglII sites of the vector pIC20R, in order to generate the plasmid pPY34. One characteristic of this plasmid is that the BamHI site obtained from the multiple cloning site is localized within the immediate vicinity of the HindIII(26238) site of the genome of the Ad5 adenovirus.

Figure 6:
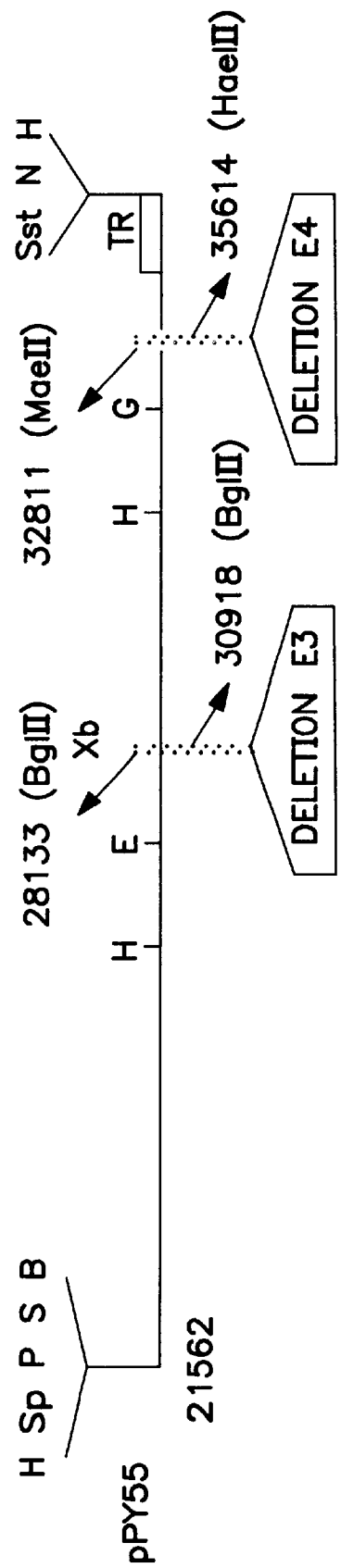
FIG. 6: Representation of the plasmid pPY55.

The BamHI(21562)-HindIII(26238) fragment of the genome of the Ad5 adenovirus obtained from the plasmid pPY17 was then cloned between the BamHI and HindIII sites of the plasmid pPY34, which generates the plasmid pPY39. The BamHI-XbaI fragment of the plasmid pPY39 prepared from a dam– context, containing the part of the genome of the Ad5 adenovirus between the BamHI(21562) and BglII(28133) sites, was then cloned between the BamHI and XbaI sites of the vector pIC19H prepared from a dam– context. This generates the plasmid pPY47 of which one advantageous characteristic is that the SalI site obtained form the multiple cloning site is localized within the vicinity of the HindIII site (FIG. 6).

c) Construction of the plasmid pPY55.

The SalI-XbaI fragment of the plasmid pPY47 prepared from a dam– context, and which contains the part of the genome of the Ad5 adenovirus stretching from the BamHI (21562) site up to the BglII(28133) site, was cloned between the SalI and XbaI sites of the plasmid pPY32, which generates the plasmid pPY55. This plasmid can be used directly to produce recombinant adenoviruses which are at least deleted in relation to the E3 region (deletion between the BglII sites localized at positions 28133 and 30818 of the genome of the Ad5 adenovirus) and in relation to the entire E4 region (deletion between the MaeII(32811) and HaeIII (35614) sites of the genome of the Ad5 adenovirus (FIG. 6).

A.2. Construction of the plasmid pE4Gal.

Figure 7:
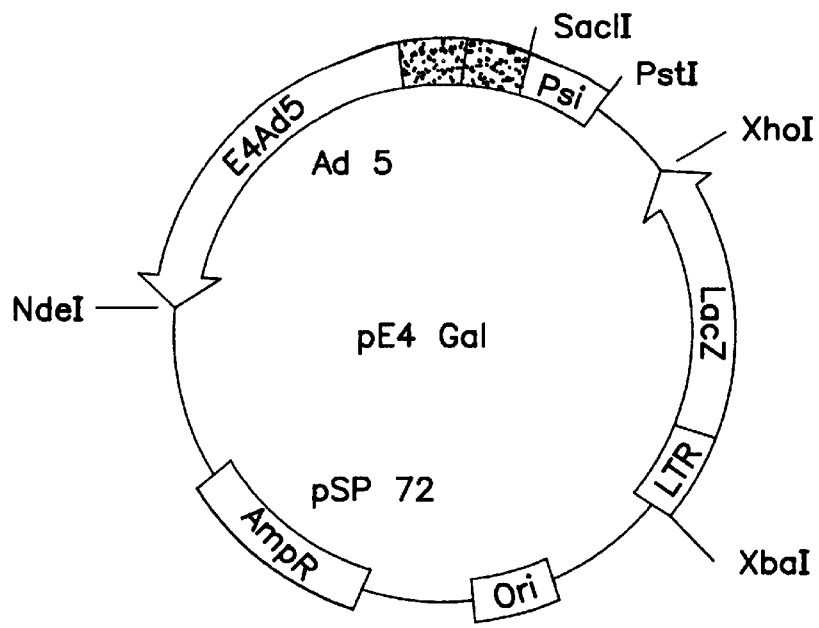
FIG. 7: Construction of the plasmid pE4Gal.

For that, a plasmid carrying the joining ITRs from Ad5, the encapsidation sequence, the E4 gene under the control of its own promoter and, as heterologous gene, the LacZ gene under the control of the LTR promoter of the RSV virus was constructed (FIG. 7). This plasmid, designated pE2Gal, was obtained by cloning and ligation of the following fragments (see FIG. 7):

HindIII-SacII fragment derived from the plasmid pFG144 (Graham et al., EMBO J.8 (1989) 2077). This fragment carries the ITR sequences from Ad5 in tandem and the encapsidation sequence: HindIII(34920)-SacII(352) fragment;

fragment from Ad5 between the SacII (localized at the level of the base pair 3827) and PstI (localized at the level of the base pair 4245) sites;

fragment of pSP 72 (Promega) between the PstI (bp 32) and SalI (bp 34) sites;

XhoI-XbaI fragment of the plasmid pAdLTR GalIX described in Stratford-Perricaudet et al. (JCI 90(1992) 626). This fragment carries the LacZ gene under the control of the LTR of the RSV virus;

XbaI (bp 40) - NdeI (bp 2379) fragment of the plasmid pSP 72;

NdeI (bp 31089) - HindIII (bp 34930) fragment in Ad5. This fragment, which is localized from the right-hand end of the Ad5 genome, contains the E4 region under the control of its own promoter. It was cloned at the NdeI (2379) site of the plasmid pSP 72 and the HindIII site of the first fragment.

This plasmid was obtained by cloning the various fragments into the indicated regions of the plasmid pSP 72. It is understood that equivalent fragments may be inserted [lacuna]

A.3 Cotransfection into the cells 293

The adenoviruses are obtained by recombination in vivo, according to the following strategies:

(i) The DNA from the Ad-dl324 virus (Thimmappaya et al., Cell 31 (1982) 543) and the plasmid pPY55, both digested with BamHI, are first ligated in vitro, and then cotransfected with the plasmid pEAGal into the cells 293.

(ii) The DNA from the Ad-dl324 virus digested with EcoRI and the plasmid pPY55 digested with BamHI are cotransfected, with the plasmid pE4Gal, into the cells 293.

(iii) The DNA from the Ad5 adenovirus and the plasmid pPY55, both digested with BamHI, are ligated and then cotransfected with the plasmid pE4Gal into the cells 293.

(iv) The DNA from the Ad5 adenovirus digested with EcoRI and the plasmid pPY55 digested with BamHI are cotransfected with pEAGal into the cells 293.

The strategies (i) and (ii) make it possible to generate a recombinant adenovirus deleted in relation to the E1, E3 and E4 regions; the strategies (iii) and (iv) make it possible to generate a recombinant adenovirus deleted in relation to the E3 and E4 regions. Moreover, it is also possible to use a cell line derived from a line expressing the E1 region, for example the line 293, and also expressing at least the open reading frames ORF6 and ORF6/7 of the Ad5 adenovirus E4 region (cf FR93 08596). The use of such lines makes it possible to avoid the use of the plasmid pE4Gal.

B/Construction of the adenovirus deleted in the IVa2, E1, E3 and E4 genes.

This adenovirus was obtained by recombination, after cotransfection into the cells 293 of the plasmid pCO2 (Example 2) and the right-hand part of an adenovirus at least deleted in relation to the E4 region, and for example the adenovirus obtained after using the plasmid pPY55 (cf. section A).

After cotransfection with calcium phosphate, the cells are harvested, disrupted by three freeze-thaw cycles in their supernatant, and then centrifuged at 4000 rpm for 10 minutes. The supernatant thus obtained is then amplified on a fresh cell culture. The viruses are then purified from plaques and their DNA is analyzed according to the Hirt method (cited above). Virus stocks are then prepared on a cesium chloride gradient.

Example 7

Figure 8:
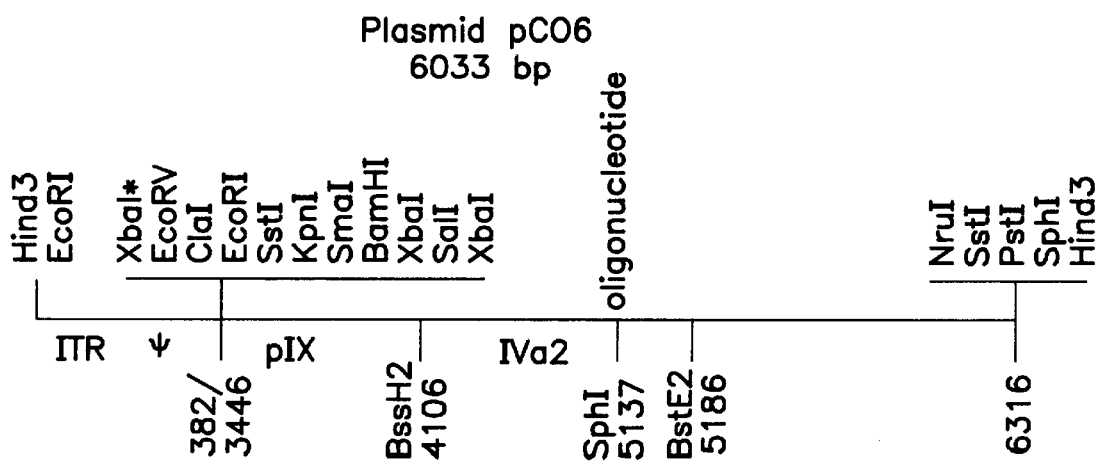
FIG. 8: Restriction map of the Hind3 fragment contained in the plasmid pCO6.

Construction of a recombinant adenovirus having a deletion in the E1, E4, IVa2 genes A—Construction of the plasmid pCO6 (FIG. 8).

A.1—Construction of the plasmid pGY38.

The Mun1-Nru1 fragment of the plasmid pCO1 containing the sequences of the Ad5 adenovirus genome ranging from bases 3924 to 6316 and especially the IVa2 gene (bases 4094 to 5719) was cloned between the Mun1 and Nru1 sites of the commercial vector pSL1180. This generates the plasmid pGY38.

A.2—Construction of the plasmid pGY39.

The following nucleotide sequence and its complementary strand were synthesized artificially by conventional molecular biology techniques:

5'- CCT TAG CCC GGG CTA AGG CAT G - 3' (SEQ ID No. 1)

Each of the strands has an Sph1 restriction site at its 3' end. This sequence was cloned into the Sph1 site of the plasmid pGY38: it introduces a stop codon into the coding part of the IVa2 gene, at the Sph1 site corresponding to the base 5141 of the Ad5 adenovirus. This generates the plasmid pGY39. In this plasmid, the IVa2 gene thus modified is inactivated: it encodes an inactive protein corresponding to the first 102 amino acids of the wild-type IVa2 protein.

A.3—Construction of the plasmid pCO6.

The Mun1-Mru1 fragment of the plasmid pGY39 was cloned between the Mun1 and Nru1 sites of the plasmid pCO1. This generates the plasmid pCO6 (FIG. 8) which contains the left-hand part of the Ad5 adenovirus up to the Hinf1 site (382), a multiple cloning site, the Sau3A (3446) - Sph1 (5141) fragment of the Ad5 adenovirus, the oligonucleotide providing a stop codon in the coding sequence of the IVa2 gene and the Sph1 (5141) - Nru1 (6316) fragment of the Ad5 adenovirus.

Figure 9:
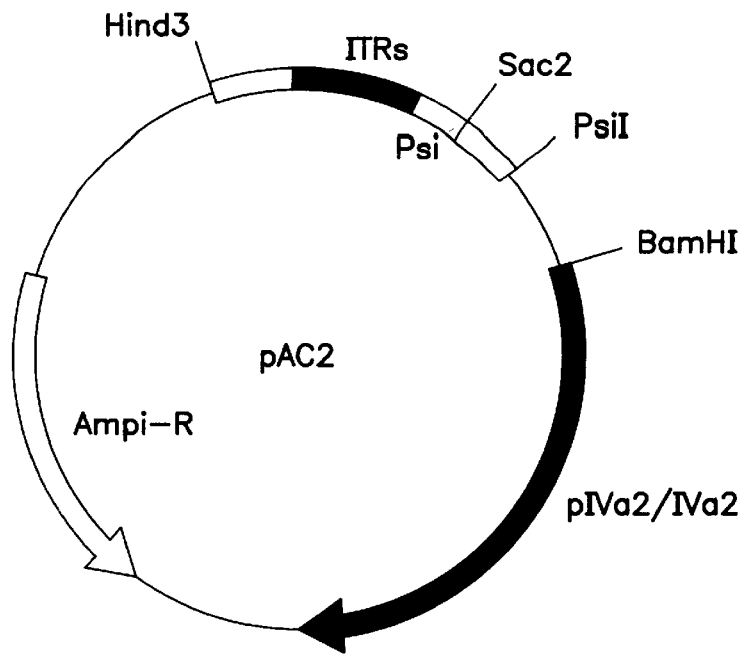
FIG. 9: Restriction map of the plasmid pAC2.

B—Construction of the plasmid pAC2 (FIG. 9).

B.1—Construction of the plasmid pSPITR.

The following fragments were cloned:

the Hind3 (34930) - Sac2 (357) fragment derived from the plasmid pFG144 (Graham et al., EMBO J.8, 1989, 2027), this fragment carried the ITR sequences of the Ad5 adenovirus in tandem and the encapsidation sequence, the Ad5 adenovirus fragment between the sites Sac2 (located at the level of base 3827 in Ad50 and Pst1 (located at the level of base 4245)

Then the plasmid pSPITR was obtained by ligation of these fragments between the Hind3 and Pst1 sites of the commercial plasmid pSP72.

B.2—Construction of the plasmid pAC2.

The Dra1-Nru1 fragment of the plasmid pCO1, which contains the sequences of the Ad5 adenovirus genome ranging from bases 4029 to 6316 and especially the IVa2 gene and its promoter, was cloned into the EcoRV site of the vector pIC20H (reference J. L. March et al. (1984) Gene, 32, 481–485). This generates the plasmid pAC1. The Bgl2-BamH1 fragment of the plasmid pAC1 was cloned into the BamH1 site of the plasmid pSPITR, which generates the plasmid pAC2 (FIG. 9).

Figure 10:
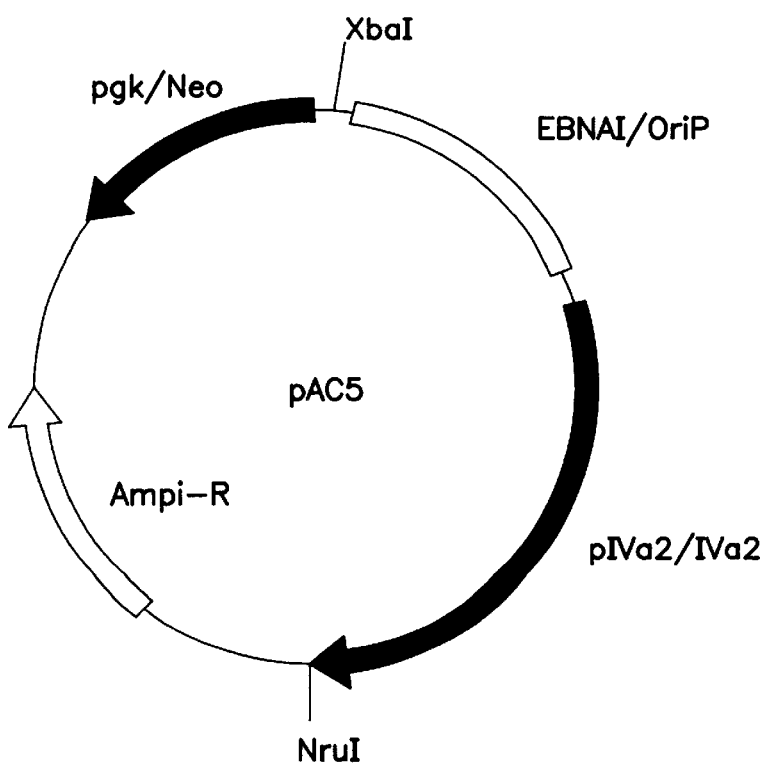
FIG. 10: Restriction map of the plasmid pAC5.

C—Construction of the plasmid pAC5 (FIG. 10).

C.1—Construction of the plasmid pAC3.

the EcoR1-Xba1 fragment of the commercial plasmid pMEP4 (Invitrogen) was ligated between the EcoR1 and Xba1 sites of the plasmid pAC1. This generates the plasmid pAC3 of which one characteristic is that it contains the ECNA1-OriP sequences and the IVa2 gene.

C.2—Construction of the plasmid pAC5.

The Sal1-Xho1 fragment of the commercial plasmid pMSCV was cloned into the Sal1 site of the vector pIC20H. This generates the plasmid pAC4 which contains the Neo gene. The Xba1-Nru1 fragment of the plasmid pAC3 was cloned between the Xba1 and Nru1 sites of the plasmid pAC4. This generates the plasmid pAC5 (FIG. 10) of which an important characteristic is that it has the Neo gene and the IVa2 gene under the control of its own promoter. Furthermore, this plasmid may replicate in eukaryotic cells because it carries the EBNA1/OriP sequences.

Figure 11:
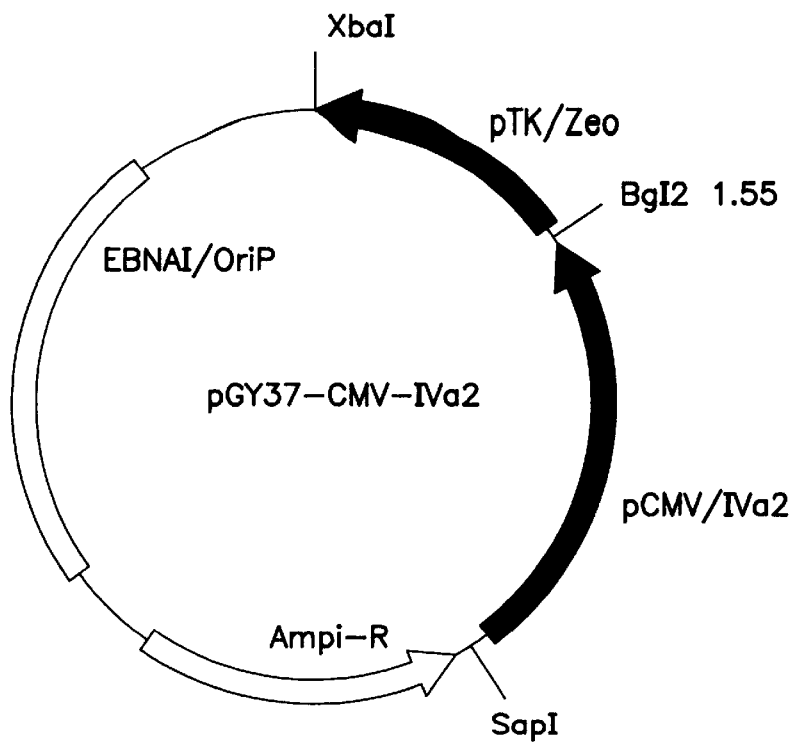
FIG. 11: Restriction map of the plasmid pGY37-TK-IVa2.

D—Construction of the plasmid pGY37-TK-IVa2 (FIG. 11).

D.1—Construction of the plasmid pGY32.

The following nucleotide sequence and its complementary strand were synthesized artificially by conventional molecular biology techniques:

5'- TCG ACG GAT CCC TTA AGG TTG ACG CCG CCA CCA TGG AAA CCA GAG GGC GAA GAC CGG CAG C -3' (SEQ ID No. 2)

It carries a restriction site for Sal1 at its 5' end and a restriction site for Eco47III at its 3' end. This sequence was inserted into the plasmid pAC1 between the Sal1 site and the Eco47III site of the beginning of the IVa2 gene which corresponds to the base 5411 of the Ad5 adenovirus sequence. This generates the plasmid pGY32 of which an important characteristic is that it has a multiple cloning site (BamH1, Af12, Hinc2) upstream of a Kazak consensus before the ATG of the IVa2 gene. Furthermore, in this construction, the intron of the IVa2 gene was suppressed.

D.2—Construction of the plasmid pGY33-TK.

The BamH1 (−110) - Hinc2 (+35) fragment of the TK promoter of the plasmid pX4B (B. Wasylyk et al., N.A.R. (19870, 15, 13, 5490) and a multiple cloning site bordered by the Sal1 and BamH1 sites were ligated and then cloned between the Sal1 and Hinc2 sites of the plasmid PGY32. This generates the plasmid pGY33-TK of which an advantageous characteristic is that it carries the IVa2 gene of intron under the control of the TK promoter.

D.3—Construction of the plasmid pGY34.

The following fragments were prepared and then ligated:
the Xba1-Pvu1 fragments of the commercial plasmid pMEP4 (5.5 kg), this fragment contains the EBNA1/OriP sequences and the 5' end of the ampicillin resistance gene,
the Pvu1-AlwN1 fragment of the commercial plasmid pMEP4 (0.8 kb), this fragment contains the 3' end of the ampicillin resistance gene and part of the replication origin,
the Xba1 and AlwN1 fragment of the plasmid pIC20H (0.8 kb), this fragment contains the end of the replication origin.

This generates the plasmid pGY34 which contains the EBNA1/OriP sequences.

D.4-Construction of the plasmid pGY36.

The BamH1 fragment of the commercial plasmid pUT614 (Cayla) was cloned into the BamH1 site of the vector pIC20H. This generates the plasmid pPY9 which contains the Zeo gene. The Xba1-EcoRV fragment of the plasmid pPY9 was cloned between the Xba1 and Nru1 sites of the vector pIC20R, which generates the plasmid pGY35. The Xba1 fragment of the plasmid pGY35 prepared in a dam⁻ context was then cloned into the Xba1 site of the plasmid pGY34. This generates the plasmid pGY36.

D.5—Construction of the plasmid pGY37-TK-IVa2 (FIG. 11).

The Bgl2-Sap1 fragment of the plasmid pGY33-TK was cloned between the Bgl2 and Sap1 sites of the plasmid pGY36. This generates the plasmid pGY37-TK-IVa2 (FIG. 11) of which an important characteristic is that it possesses the Zeo gene and the Iva2 gene, without intron, under the control of the TK promoter. Furthermore, this plasmid may replicate in eukaryotic cells because it carries the EBNA1/OriP sequences.

Figure 12:
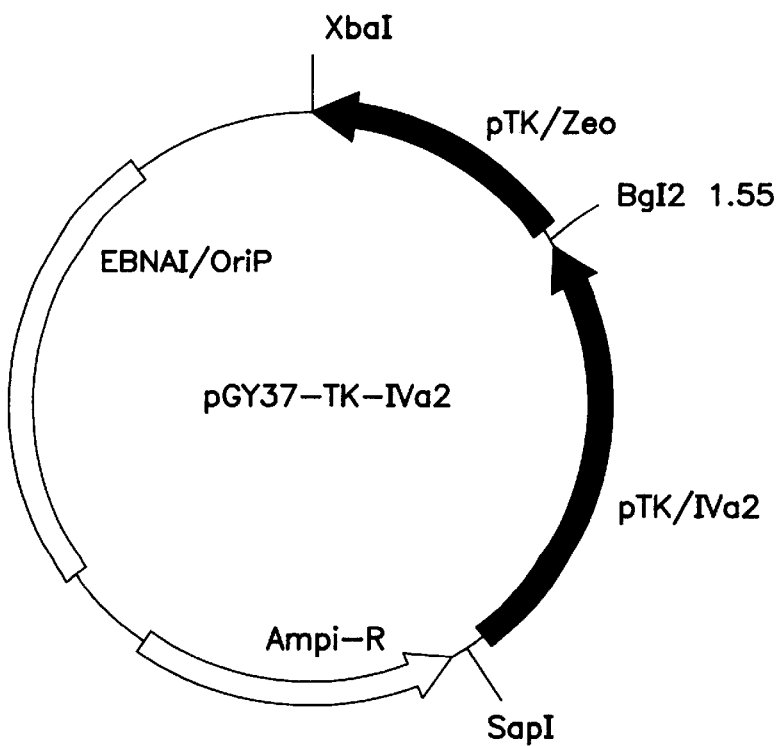
FIG. 12: Restriction map of the plasmid pGY37-CMV-IVa2.

E—Construction of the plasmid pGY37-CMV-IVa2 (FIG. 12).

E.1—Construction of the plasmid pGY33-CMV.

The Bgl2-Afl2 fragment of the commercial plasmid pCI (Promega) was cloned between the BamH1 and Af12 sites of the plasmid PGY32. This generates the plasmid pGY33-CMV of which a characteristic of interest is that it carries the IVa2 gene free of intron under the control of the CMV promoter.

E.2—Construction of the plasmid pGY37-CMV-IVa2 (FIG. 12).

The Bgl2-Sap1 fragment of the plasmid pGY33-CMV was cloned between the Bgl2 and Sap1 sites of the plasmid pGY36. This generates the plasmid pGY37-CMV-IVa2 (FIG. 12) of which an important characteristic is that it has the Zeo gene and the IVa2 gene, without intron, under the control of the CMV promoter. Furthermore, this plasmid may replicate in eukaryotic cells because it carries the EBNA1/OriP sequences.

F—Construction of the cell clones expressing the IVa2 region of the Ad5 adenovirus.

Various types of cell lines transcomplementing the IVa2 function were constructed in $E1^+$ cells (cells 293 or 293 E4)

(a) The plasmid pAC5 was transfected into the cells 293 in the presence of calcium phosphate, the cell clones carrying the replicative plasmid pAC5 were selected in the presence of geneticin (Sigma, 400 µg/ml).

(b) The plasmid pGY37-TK-IVa2 was transfected into the cells in the presence of calcium phosphate, the cell clones carrying the replicative plasmid pGY37-TK-IVa2 were selected in the presence of phleomycin (Cayla, 15 µg/ml for the cells 293 and 30 µg/ml for the cells 293 E4).

(c) The plasmid pGY37-CMV-IVa2 was transfected into the cells in the presence of calcium phosphate, the cell clones carrying the replicative plasmid pGY37-CMV-IVa2 were selected in the presence of phleomycin (Cayla, 15 µg/ml for the cells 293 and 30 µg/ml for the cells 293 E4). More precisely, in each of these three cells, cell sin dishes 5 cm in diameter were transfected by 1 to 5 µg of plasmid in the presence of calcium phosphate. After transfection of the cells, these are washed, and then the culture medium (MEM, Sigma) supplemented with foetal calf serum (7% final) is added and the cells are incubated for 24 hours. The next day, the cells are selected in the presence of geneticin or phleomycin. The geneticin or the phleomycin is changed every three days and the selectable clones appear after about three weeks. When all the non-transfected cells have died, only the transfected cells divide, generating cell clones. When the cell clones are sufficiently large to be visible with the naked eye, they are individually transferred into the culture wells of a "24 slot" culture plate. Each clone is then progressively amplified, in the presence of geneticin or phleomycin, first in the wells of a "12 slot", and then "6 slot" culture plate so as then to be amplified in cell culture dishes.

G—Construction of a recombinant adenovirus carrying a deletion in the E1-IVa2-E4 genes.

G.1—Construction of an adenovirus ΔE1-ΔIVa2-ΔE4 by cotransfection of a helper virus carrying the IVa2 gene.

For example, it was possible to prepare the adenovirus ΔE1-ΔIVa2-ΔE4 according to the following two procedures:

(a) The DNA of a ΔE1–ΔE4 virus digested with Cla1 (for example AdRSBβgal-dl1004, AdRSBβgal-dl1007 or AdRSVβgal-dl11014 described in "Efficient dual transcomplementation of adenovirus E1 and E4 regions from a 293-derived cell line expressing a minimal E4 functional unit" by P. YEH et al., J. Virology, in press), the plasmid pCO2 DNA digested with Xmn1 and the helper virus pAC2 DNA were cotransfected into 293 E4 cells in the presence of calcium phosphate.

(b) The DNA of a ΔE1–ΔE4 virus digested with Cla1, the plasmid pCO6 DNA digested with Xmn1 and the helper virus pAC2 DNA were cotransfected into the 293 E4 cells in the presence of calcium phosphate.

G.2–Construction of an adenovirus ΔE1-ΔIVa2-ΔE4 in cell lines transcomplementing the IVa2 and E4 functions.

In the cell clones expressing the IVa2 and E4 regions of the Ad5 adenovirus and resistant to phleomycin, it was possible to prepare the adenovirus ΔE1-ΔIVa2-ΔE4 according to the following two procedures:

(a) The DNA of a ΔE1–ΔE4 virus digested with Cla1 and the plasmid pCO2 DNA digested with Xmn1 were cotransfected into the cells in the presence of calcium phosphate.

(b) The DNA of a ΔE1–ΔE4 virus digested with Cla1 and the plasmid pCO6 DNA digested with Xmn1 were cotransfected into the cells in the presence of calcium phosphate.

We claim:

1. A replication defective recombinant adenovirus comprising a nonfunctional IVa2 gene, wherein the IVa2 gene is made nonfunctional by substitution, deletion, or addition of one or more bases within the IVa2 gene coding region.

2. The adenovirus according to claim 1, wherein the IVa2 gene is made nonfunctional by deletion of one or more bases.

3. The adenovirus according to claim 1, wherein the IVa2 gene is made nonfunctional by partial deletion.

4. The adenovirus according to claim 1, wherein the IVa2 gene is made nonfunctional by deletion of a fragment comprising nucleotides 4106 to 5186.

5. The adenovirus according to claim 1, which further comprises a heterologous nucleic acid sequence.

6. The adenovirus according to claim 1, which further comprises a deletion in all or part of the E1 gene.

7. A replication defective adenovirus comprising a first deletion in the E1 gene and a second deletion in the IVa2, wherein the first deletion comprises nucleotides 382 to 3446 of the E1 gene, and wherein the second deletion comprises nucleotides 4106 to 5186 of the IVa2 gene.

8. The adenovirus according to claim 1, which further comprises a deletion in all or part of the E4 gene.

9. The adenovirus according to claim 1, which further comprises a deletion in all or part of the E1 gene and the E3 gene.

10. The adenovirus according to claim 8, which further comprises a deletion in all or part of the E1 gene.

11. The adenovirus according to claim 9, which further comprises a deletion in all or part of the E4 gene.

12. The adenovirus according to claim 11, which further comprises a deletion in all or part of the L5 gene.

13. The adenovirus according to claim 1, wherein the adenovirus is of human origin.

14. The adenovirus according to claim 13, wherein the adenovirus is classified in group C.

15. The adenovirus according to claim 14, wherein the group C adenovirus is a type 2 (Ad2) or type 5 (Ad5) adenovirus.

16. The adenovirus according to claim 1, which further comprises the E3 gene encoding the gp19K protein under control of a heterologous promoter.

17. The adenovirus according to claim 5, wherein the heterologous nucleic acid sequence is a therapeutic gene or a gene encoding an antigen.

18. The adenovirus according to claim 5, wherein the heterologous nucleic acid sequence comprises a secretory sequence.

19. The adenovirus according to claim 1, further comprising a deletion extending from nucleotides 382 to 3446 of the E1 gene.

20. A plasmid pCO2 as set forth in FIG. 4.

21. A plasmid pCO6 as set forth in FIG. 8.

22. A plasmid pAC5 as set forth in FIG. 10.

23. A plasmid pGY37-TK-IVa2 as set forth in FIG. 11.

24. A plasmid pGY37-CMV-IVa2 as set forth in FIG. 12.

25. The adenovirus according to claim 1, which further comprises a functional E3 gene operably linked to a heterologous promoter.

26. The adenovirus according to claim 25, wherein the E3 gene encodes adenovirus gp19K protein.

* * * * *

UNITED STATES PATENT AND TRADEMARK OFFICE
CERTIFICATE OF CORRECTION

PATENT NO. : 6,200,798 B1  
DATED : March 13, 2001  
INVENTOR(S) : Yeh et al.

Page 1 of 1

It is certified that error appears in the above-identified patent and that said Letters Patent is hereby corrected as shown below:

<u>Column 20, claim 4,</u>  
Line 3, "claim 1" should read -- claim 3 --.

Signed and Sealed this

Eighteenth Day of December, 2001

Attest:

Attesting Officer

JAMES E. ROGAN  
*Director of the United States Patent and Trademark Office*